(12) United States Patent
Condie et al.

(10) Patent No.: US 7,218,968 B2
(45) Date of Patent: May 15, 2007

(54) USER INTERFACE FOR PROGRAMMING RATE RESPONSE TECHNICAL FIELD

(75) Inventors: Catherine R. Condie, Shoreview, MN (US); Marilyn C. Rochat, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 588 days.

(21) Appl. No.: 10/284,901

(22) Filed: Oct. 31, 2002

(65) Prior Publication Data
US 2004/0088020 A1    May 6, 2004

(51) Int. Cl.
*A61N 1/05* (2006.01)
*A61B 5/04* (2006.01)

(52) U.S. Cl. ............................ 607/59; 607/30; 600/523
(58) Field of Classification Search ................... 607/17, 607/25, 27, 30, 32, 59, 60; 600/523, 525
See application file for complete search history.

(56) References Cited

U.S. PATENT DOCUMENTS

| 4,791,936 A | * | 12/1988 | Snell et al. | 600/510 |
|---|---|---|---|---|
| 5,292,341 A | | 3/1994 | Snell | 607/30 |
| 5,330,513 A | | 7/1994 | Nichols et al. | 607/32 |
| 5,421,830 A | | 6/1995 | Epstein et al. | 607/30 |
| 5,487,754 A | * | 1/1996 | Snell et al. | 607/27 |
| 5,509,927 A | | 4/1996 | Epstein et al. | 607/32 |
| 5,514,162 A | * | 5/1996 | Bornzin et al. | 607/19 |
| 5,713,937 A | | 2/1998 | Nappholz et al. | 607/30 |
| 5,792,198 A | * | 8/1998 | Nappholz | 607/18 |
| 5,833,623 A | * | 11/1998 | Mann et al. | 600/523 |
| 5,948,005 A | | 9/1999 | Valikai et al. | 607/32 |

FOREIGN PATENT DOCUMENTS

WO    WO 01/24875 A1    4/2001

* cited by examiner

*Primary Examiner*—Robert E. Pezzuto
*Assistant Examiner*—Tammie K. Heller
(74) *Attorney, Agent, or Firm*—Paul H. McDowall; Girma Wolde-Michael

(57) ABSTRACT

A programmer including a user interface, and techniques for programming a rate responsive implantable medical device using such a programmer and user interface are presented. The programmer may retrieve currently programmed rate response parameters and optimization target values of an implantable medical device. The programmer may display the currently programmed rate response parameters and optimization target values via a user interface. The programmer may also generate a current rate response curve and a current target rate histogram, and display the current rate response curve and current target rate histogram via the user interface. The programmer may receive changes to the displayed currently programmed rate response parameters and/or target values made by a user via the user interface, generate a pending rate response curve and/or a pending target rate histogram based on these changes, and display the pending rate response curve and/or pending target rate histogram via the user interface.

42 Claims, 12 Drawing Sheets

USER INTERFACE FOR PROGRAMMING RATE RESPONSE TECHNICAL FIELD

TECHNICAL FIELD

The invention relates to rate responsive therapy in general and, more particularly, to techniques for programming the rate responsive behavior of an implantable medical device.

BACKGROUND

Implantable medical devices that are rate responsive monitor one or more physiological parameters of patients in which they are implanted, and adjust the rate of one or more stimulation outputs based on changes in these physiological parameters. For example, a rate responsive pacemaker may monitor one or more physiological parameters that indicate an activity level of a patient, such as patient motion, respiration, temperature, blood pressure, blood pH, blood oxygen and/or the lengths of various intervals within an electrocardiogram of the patient. A rate responsive pacemaker adjusts the rate at which pacing pulses are delivered to the heart of the patient in the absence of a sensed depolarization, by adjusting one or more escape intervals based on the changes in these physiological parameters. In general, a rate responsive pacemaker attempts to ensure that the heart rate of a patient is appropriate for the current activity level of the patient.

The rate response behavior of a rate responsive pacemaker is controlled by a number of programmed parameters stored within the pacemaker. A physician, clinician, or the like, may use a programmer that communicates with the pacemaker to program or reprogram these parameters. For example, a physician or clinician may specify ranges of heart rates and the rate response, i.e., the relationship between the output of the one or more sensors and the rate at which pacing pulses are delivered to a patient in the absence of a sensed depolarization, within those ranges. The programmer may direct the pacemaker to change the values of the parameters stored therein in response to the input provided by the physician or clinician. For some physicians and clinicians, the use of existing programmers and associated techniques to program these parameters has proven to be unintuitive, and, in some cases, confusing.

Often, in order to arrive at an appropriate rate response for a particular patient, a physician or clinician first programs the pacemaker, and then subjects the patient to an exercise test in order to determine the effectiveness of the current parameters at a variety of activity levels. The pacemaker may store data that indicates its rate response performance during the exercise test, and the programmer may retrieve this information and display it to the physician in some form such that the physician may evaluate it. In some cases, this process must be repeated multiple times before an appropriate rate response for that particular patient is achieved. Further, as the condition of the patient and/or the pacemaker changes, it may be determined on a follow-up visit to the clinic that the previously programmed parameters are no longer effective, requiring that the physician or clinician again subject the patient to this programming process.

Pacemakers that automatically optimize rate response parameters may allow physicians and patients to avoid multiple programming and exercise test iterations. In general, pacemakers that optimize rate response receive one or more performance targets from the physician, such as a target percentage of time for the sensor indicated rate to be within a particular range of rates, determine whether the performance targets are being met, and, if necessary, adjust the parameters to meet the targets. However, it may take two or more weeks for a pacemaker to reach the optimized rate response, and for the patient to feel better. Moreover, after this delay, the optimized rate response may still not be adequate if the physician erred in choosing the performance targets.

SUMMARY

In general, the invention is directed to a programmer including a user interface, and techniques for programming a rate responsive implantable medical device using such a programmer and user interface. The programmer may interrogate an implantable medical device to retrieve programmed rate response parameters and optimization target values of the implantable medical device. The programmer may display the currently programmed rate response parameters and optimization target values via a user interface. The programmer may also generate a current rate response curve and a current target rate histogram, and display the current rate response curve and current target rate histogram via the user interface.

The programmer may receive changes to the displayed currently programmed rate response parameters and/or target values made by a user via the user interface, generate a pending rate response curve and/or a pending target rate histogram based on these changes, i.e., pending parameters or target values, and display the pending rate response curve and/or pending target rate histogram via the user interface. A user may accept the pending parameters and/or optimization target values via the user interface, and the programmer may reprogram the implantable medical device with the pending parameters or optimization target values based on the acceptance.

In one embodiment, the invention is directed to a method that includes receiving currently programmed rate response parameters and at least one currently programmed optimization target value from an implantable medical device, and displaying the currently programmed parameters and at least one target value via a user interface. The method further includes generating a current rate response curve based on the parameters and a current target rate histogram based on the parameters and at least one target value, and displaying the curve and the histogram via the user interface.

In another embodiment, the invention is directed to a computer-readable medium containing instructions. The instructions cause a programmable processor to receive currently programmed rate response parameters and at least one currently programmed optimization target value from an implantable medical device, and display the currently programmed parameters and at least one target value via a user interface. The medium also includes instructions that cause a processor to generate a current rate response curve based on the parameters and a current target rate histogram based on the parameters and at least one target value, and display the curve and the histogram via the user interface.

In another embodiment, the invention is directed to a device that includes a transceiver to communicate with an implantable medical device and a processor. The processor receives currently programmed rate response parameters and at least one currently programmed optimization target value from the implantable medical device via the transceiver, and displays the currently programmed parameters and at least one target value via a user interface. The processor also generates a current rate response curve based on the parameters and a current target rate histogram based on the parameters and at least one target value, and displays the curve and the histogram via the user interface.

In another embodiment, the invention is directed to a method that includes receiving at least one rate response optimization target value, generating a target rate histogram based on the at least one received target value, and displaying the target rate histogram via a user interface.

In another embodiment, the invention is directed to a computer-readable medium containing instructions. The instructions cause a programmable processor to receive at least one rate response optimization target value, generate a target rate histogram based on the at least one received target value, and display the target rate histogram via a user interface.

The invention is capable of providing one or more advantages. For example, a programmer that displays a current rate response curve or current target rate histogram via a user interface may allow the user to more easily visualize the current programming of an implantable medical device, and the effect of the current programming on a patient in whom the medical device is implanted. Further, a programmer that displays a pending rate response curve or pending target rate histogram via a user interface based on pending changes to the programming made by a user via the user interface may allow the user to more easily visualize the effect that those pending changes would have on the rate response of an implantable medical device and a patient in whom the medical device is implanted, if they were accepted and used to reprogram the implantable medical device. In some embodiments, the programmer displays current and pending curves or histograms side-by-side, further increasing the ability of a user to understand the effect of pending changes to the programming of the implantable medical device. A user of such a programmer may evaluate the effect of these changes before submitting them to the implantable medical device, i.e. without reprogramming the implantable medical device with the changes, and without an exercise test.

Some programmer embodiments may provide a user interface with slider-bar fields, arrows, or buttons indicating "more" and "less" aggressive rate response. Such embodiments provide an intuitive interface for a user to adjust the aggressiveness of the rate response of an implantable medical device. Using such interfaces, a user need not understand the relationship between various parameters that control the rate response of the implantable device in order to effectively adjust the rate response of the implantable medical device.

Some programmer embodiments capable of rate response optimization may associate changes in optimization target values with changes in other programmed parameters that control the rate response of the implantable medical device. When the user intends to change an optimization target value, the corresponding change in the programmed parameters will advantageously bring them closer to the values that the implantable medical device would arrive at through optimization based on the changed optimization target values. Thus, at the time of programming, the rate response of the implantable medical device will be closer to the eventual optimized response, allowing the patient to more quickly feel the effect of the changes, and the user to more quickly evaluate whether the changes made are effective.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
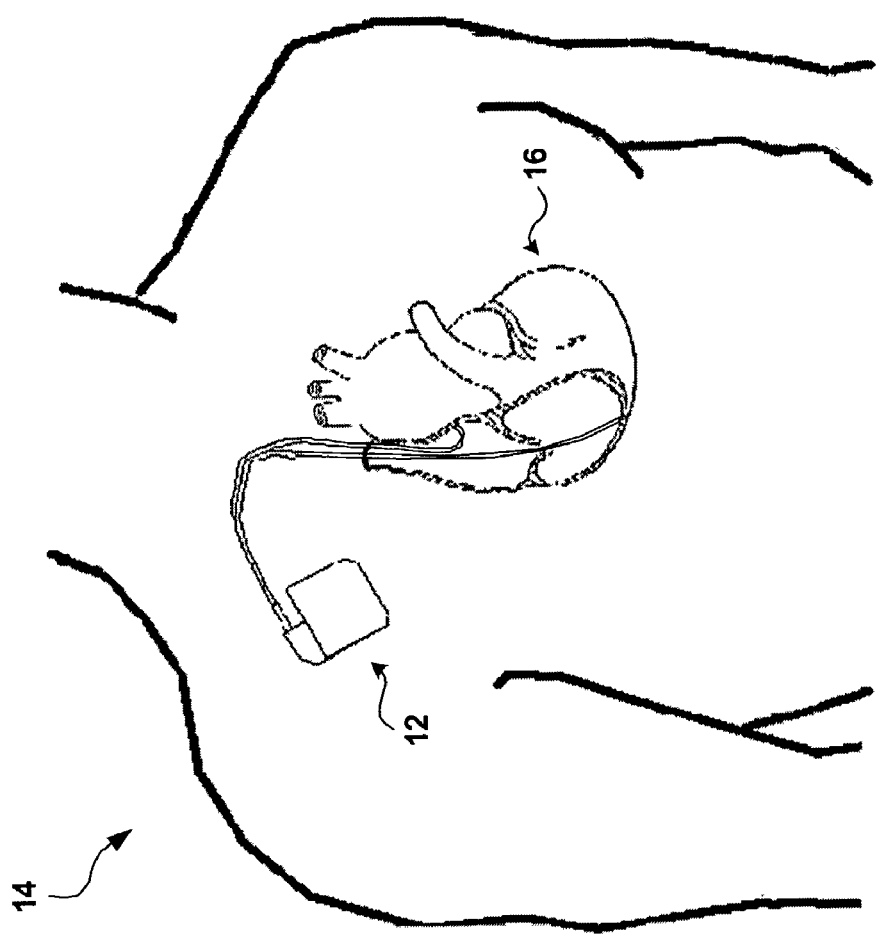
FIG. 1 is a perspective diagram illustrating a programmer to program the rate response behavior of an implantable medical device.
Figure 1:
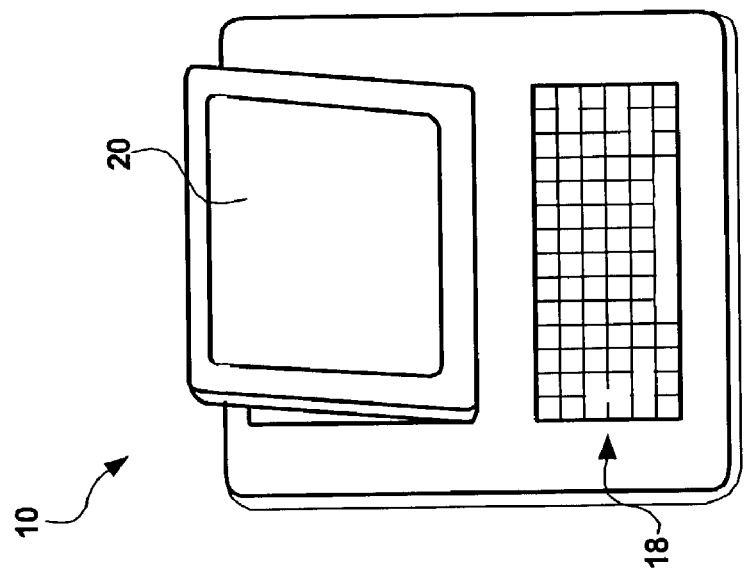

FIG. 1 is a perspective diagram illustrating a programmer 10 to program the rate response of an implantable medical device (IMD) 12 implanted within a patient 14. As illustrated in FIG. 1, IMD 12 may be a rate responsive pacemaker or rate responsive implantable cardioverter-defibrillator. Embodiments of programmer 10 that interact with a rate-responsive pacemaker embodiment of IMD 12 will be described herein.

However, the invention is not so limited, and may be applied to any programmer 10 for programming any rate-responsive medical device.

A user (not shown) of programmer 10, such as a clinician or physician, interacts with programmer 10 and IMD 12 via a user interface. A user may interact with the user interface provided by programmer 10 via a keyboard 18 and a monitor 20, which may for example, be a CRT monitor, LCD monitor, LED monitor, or the like. Programmer 10 may also include a pointing device, such as a mouse, via which a user may interact with the user interface. Programmer 10 is in wireless communication with IMD 12. Programmer 10 may, for example, communicate with IMD 12 by wireless transmission via a programming head (not shown) placed over IMD 12 and telemetry circuits of IMD 12 as is known in the art.

IMD 12 may include a memory to store data reflecting electrical activity sensed in heart 16, the output of various other sensors of IMD 12, such as one or more sensors used to control the rate response of IMD 12, and the rate response of IMD 12 over time. The rate response of IMD 12 is controlled by a number of programmed parameters stored by IMD 12. IMD 12 may also provide for the optimization of some of these parameters based on one or more optimization target values provided by a user and stored by IMD 12. Programmer 10 may interrogate IMD 12 to retrieve the data, and the currently programmed parameters and optimization target values stored by IMD 12, and display some or all of these items to a user via the user interface provided by programmer 10. A user may also program or reprogram the rate response of IMD 12 via the user interface by, for example, providing or adjusting rate response parameters or target values. The user interface provided by programmer 10 may provide a number of advantages which may simplify the programming or reprogramming of IMD 12 by a user, as will be discussed in greater detail below.

IMD 12 may deliver pacing pulses to heart 16 of patient 14 on demand, or as otherwise programmed, as controlled by a rate control signal which is determined based on the output of the one or more physiological sensors (not shown). IMD 12 may include one or more physiological sensors that generate output signals that vary based on the activity level of patient 14. For example, IMD 12 may include a sensor that detects the motion of the patient, e.g., an activity sensor or accelerometer, which may be a piezoelectric crystal, a sensor that monitors respiration, e.g., a sensor that measures thoracic impedance, a sensor that monitors patient temperature, a sensor that monitors blood pressure at some location within the circulatory system of the patient, a sensor that monitors the pH of blood of the patient, a sensor that monitors the level of oxygen within the blood of the patient, or IMD 12 may monitor lengths of various intervals within an electrocardiogram of the patient. In an exemplary embodiment, IMD 12 is a dual sensor rate responsive pacemaker that includes a sensor to detect motion of patient 14 and a sensor that monitors the respiration of patient 14. In such an embodiment, IMD 12 may determine the weights or relative contributions of the signals generated by each sensor to the rate control signal used to determine the sensor indicated heart rate, i.e., the rate that IMD 12 will pace heart 16 at in the absence of a sensed ventricular depolarization.

As mentioned above, IMD 12 determines sensor indicated rate, i.e., the rate response of IMD 12 based on a number of programmed parameters. These programmed parameters may be received from a user via the user interface of programmer 10, and stored in a memory of IMD 12. These programmed parameters may include rate limits, such as a lower rate (LR) and an upper sensor rate (USR). The LR and USR are the minimum and maximum sensor indicated rates available to IMD 12, i.e., the minimum and maximum rates at which IMD 12 will pace heart 16, respectively.

These programmed parameters may also include one or more setpoint values that indicate a currently programmed or selected curve used to determine the sensor indicated rate based on the output of the sensors. IMD 12 may store a family of curves or look-up tables that relate sensor output to sensor indicated rate. These curves provide varying levels of rate response at a given output of the sensors, i.e., have varying slopes from the LR to the USR. The greater the slope of a curve is, the more aggressive the rate response of IMD 12 employing that curve across a range of sensor outputs will be. IMD 12 determines a sensor indicated rate for a sensor output by comparing the sensor output to the currently programmed or selected curve. Through the selection of curves or tables, a user may provide a customized rate response for patient 14 that is appropriate for the condition and overall activity level of patient 14 via IMD 12.

In some embodiments, IMD 12 may be a dual-slope rate responsive pacemaker. Programmed parameters for a dual-slope embodiment of IMD 12 also include a third rate limit that falls between the LR and USR. This third rate limit may divide the effective rate range of such an embodiment of IMD 12 into two rate ranges, from the LR to the third rate, and from the third rate to the USR.

IMD 12 may provide a first rate response within the range from the LR to the third rate, and a second rate response within the range form the third rate to the USR. In other words, IMD 12 may maintain a separate family of curves with associated setpoint values for each of these ranges, and a user may select the curve within each range by programming a setpoint for each range. Through the selection of curves or tables in a dual-slope device, a user may provide a customized rate response for patient 14 via IMD 12 that is not only appropriate for the condition and overall activity level of patient 14, but is appropriate within the distinct ranges of activity levels and heart rates.

A user may select a curve for the range between the LR and the third rate that provides a desired rate response during normal daily activities of patient 14, such as getting into and out of bed, walking around the house, and the like. Thus, the third rate may be referred to as the activities of daily living rate (ADLR). The range of rates between the LR and the ADLR may be referred to as the ADL range. The user may select a curve for the range between the ADLR and USR that provides a desired rate response during more strenuous activities, such as exercising. The range between the ADLR and USR may be referred to as the exertion range.

The rate response of IMD 12 may also be controlled by parameters that control how quickly IMD 12 reaches a sensor indicated rate. An attack constant may control how quickly IMD 12 can increase the sensor indicated rate in response to increased output of the sensors. A decay constant may control how slowly IMD 12 can decrease the sensor indicated rate in response to decreased output of the sensors.

As mentioned above, IMD 12 may optimize some of these programmed parameters, and thus the rate response of IMD 12, based on one or more optimization target values received from a user and stored in a memory of IMD 12. In general, IMD 12 optimizes the rate response parameters by adjusting setpoint values, i.e., selecting different curves, in order to meet the optimization target value. In some embodiments of IMD 12, an optimization target value may be a percentage of time that IMD 12, through changes made to programmed parameters via the optimization program, will cause the sensor indicated rate to be within a rate range. Some dual-slope embodiments of IMD 12 may receive two optimization target values from a user. The first optimization target value may be a percentage of time that IMD 12 will cause the sensor indicated rate to be within the range from the ADLR to the USR, and may be referred to as the ADL percentage. The second optimization target value may be a percentage of time the IMD 12 will cause the sensor indicated rate to be at the USR, and may be referred to as the USR percentage.

As will be described in greater detail below, programmer 10, via the user interface, provides a user with a depiction of the current rate response of IMD 12 in the form of a curve that relates activity level to sensor indicated rate based on currently programmed parameters received from IMD 12, and may provide a depiction of a current target distribution of the sensor indicated rate over time that is to be or has been caused by currently programmed optimization target values. Programmer 10 may also provide a pending rate response curve, and a pending target distribution of the sensor indicated rate via the user interface based on changes to parameters and/or target values made by a user via the user interface. The heart rate distributions may be displayed as rate histograms that show estimated percentages of time IMD 12 will cause the heart rate to be in discrete rate ranges, or bins, based on the currently programmed parameters and optimization target values.

Display of the current rate response curve and current target rate histogram by programmer 10 via the user interface may allow the user to more easily visualize the current programming of IMD 12, and its effect on patient 14. Display of pending rate response curve and target rate histograms by programmer 10 may allow the user to more easily visualize the effect of the changes made on the rate response of IMD 12 and patient 14, making programming IMD 12 more intuitive for the user. Moreover, the user may evaluate the effect of these changes before submitting them to IMD 12, i.e. without reprogramming IMD 12 with the changed parameters or target values, and without an exercise test.

Figure 2:
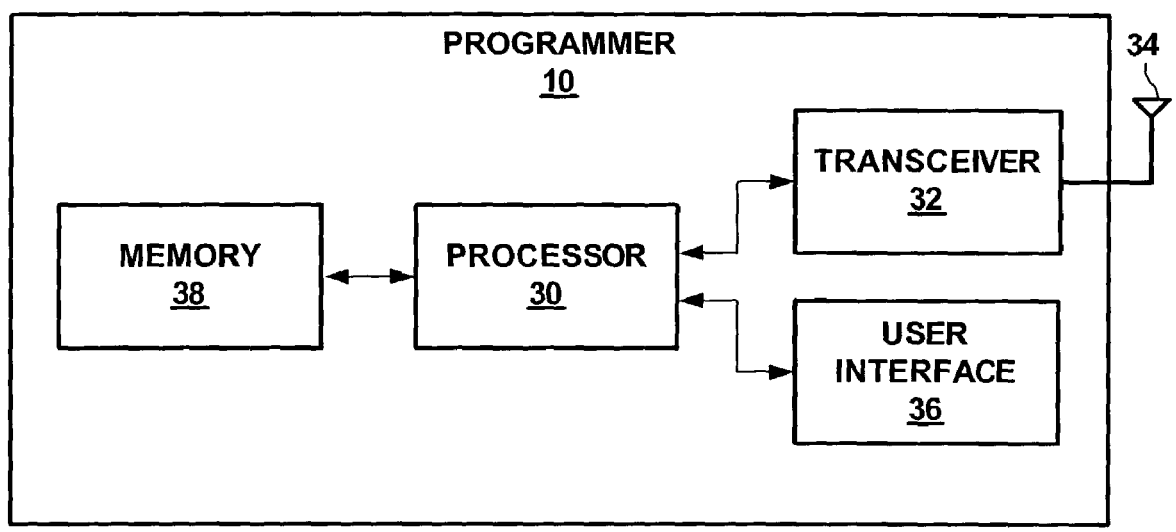
FIG. 2 is a block diagram illustrating the programmer of FIG. 1 in greater detail.

FIG. 2 is a block diagram illustrating programmer 10 in greater detail. As shown in FIG. 2, programmer 10 includes a processor 30, a transceiver 32, and an antenna 34. As mentioned above, programmer 10 may be in wireless communication with IMD 12. Processor 30 may receive data collected by IMD 12, currently programmed rate response parameters, and currently programmed optimization target values from IMD 12, and may reprogram IMD 12 by providing new parameters and/or optimization target values to IMD 12 via transceiver 32 and antenna 34. Antenna 34 may correspond to the programming head that may be placed over heart 16 as described above with reference to FIG. 1.

As discussed above, programmer 10 provides a user interface 36 by which a user of programmer 10, such as a clinician or physician, interacts with programmer 10 and IMD 12. User interface 36 may be a graphical user interface displayed on monitor 20, and a user may interact with user interface 36 via monitor 20, keyboard 18, and/or a pointing device, illustrated in FIG. 1. Processor 30 may provide user interface 36 as described herein. A memory 38 may store program code that causes processor 30 to provide user interface 36 as described herein, and the functionality ascribed to user interface 36 herein. Memory 38 may include any fixed or removable magnetic or optical media, such as RAM, ROM, CD-ROM, hard or floppy magnetic disks, EEPROM, or the like.

As will be described in greater detail below, processor 30 may display data collected by IMD 12, currently programmed rate response parameters and optimization target values retrieved from IMD 12 via user interface 36. Processor 30 may also generate a current rate response curve and a current target rate histogram, and display the current rate response curve and current target rate histogram via user interface 36. Processor 36 may receive changes to the currently programmed rate response parameters and/or target values made by a user via user interface 36, generate a pending rate response curve and/or a pending target rate histogram based on these changes, and display the pending rate response curve and/or pending target rate histogram via user interface 36. A user may accept the changes made to the programmed parameters and/or optimization target values via user interface 36, and programmer 10 may direct IMD 12 to change the parameters or optimization target values stored within a memory of IMD 12 based on the acceptance.

FIGS. 3A–3F are diagrams illustrating an exemplary embodiment of user interface 36 that may be provided by processor 30. The embodiment of user interface 36 illustrated in FIGS. 3A–3F is an embodiment that may be provided by processor 30 to allow a user to program or reprogram a dual-slope rate responsive pacemaker embodiment of IMD 12. It is to be understood, however, that the invention is not limited to embodiments of user interface 36 for programming or reprogramming dual-slope rate responsive pacemakers. Nor is the invention limited to embodiments of user interface 36 that display the information that user interface 36 is depicted as displaying in FIGS. 3A–3F, that display the information in the same manner as user interface 36 is depicted as displaying in FIGS. 3A–3F, or that provide buttons, drop-down menus, text boxes, slider-bars, or the like in the same manner as user interface 36 is depicted as providing in FIGS. 3A–3F. Moreover, embodiments of user interface 36 consistent with the invention may provide additional screens, windows, fields, functionality, and the like, not illustrated in FIGS. 3A–3F.

Figure 3A:
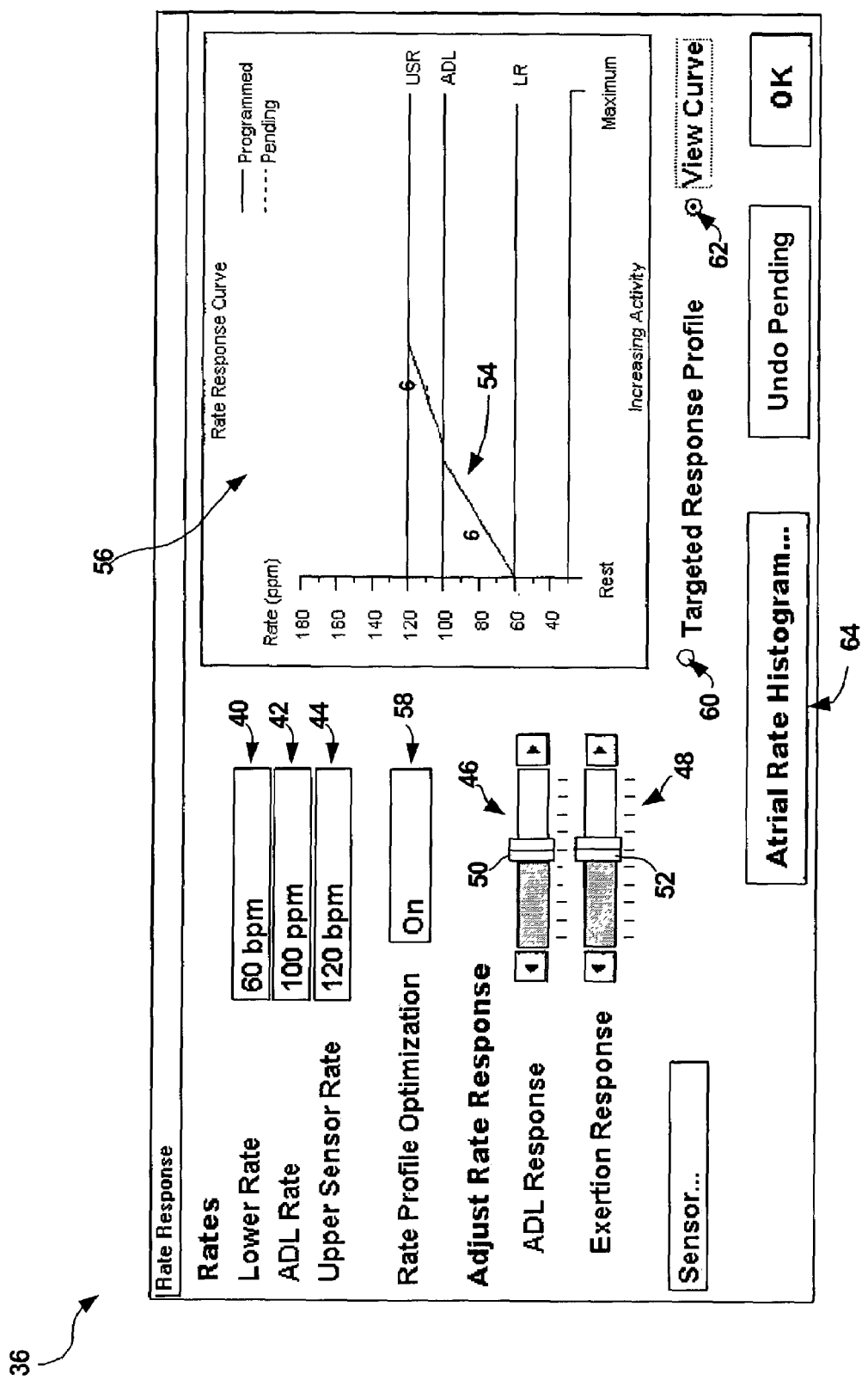
FIGS. 3A–3F are diagrams illustrating an exemplary user interface that may be provided by the programmer of FIGS. 1 and 2.

FIG. 3A illustrates user interface 36 after processor 30 has retrieved data, currently programmed rate response parameters and, in some cases, currently programmed optimization target values stored within a memory of IMD 12. As mentioned above, processor 30 may display some of the currently programmed parameters via user interface 36. For example, as shown in FIG. 3A, processor 30 may display the programmed rate limits, e.g., the LR, ADLR, and USR, within fields 40–44. Fields 40–44 may comprise drop-down menus, text boxes, or drop-down menus with text boxes, and a user may make changes to the programmed rate limits displayed in fields 40–44 by clicking on and/or typing within fields 40–44 using a mouse and/or keyboard 18. Although not shown in FIG. 3A, user interface 36 may also display and allow a user to change additional programmed parameters via fields similar to fields 40–44, such as acceleration and decay constants.

Processor 30 also generates and displays current rate response curve values for the ADL range, which includes rates from the LR to the ADLR, and the exertion range, which includes rates from the ADLR to the USR. The rate response curve values correspond to and are generated based on the currently programmed setpoints retrieved from IMD 12, which in turn correspond to the currently selected curve from the family of curves for each range. Although each family of curves stored by IMD 12 may include numerous curves, and thus the number setpoint values may be numerous, processor 30 may convert the setpoint values retrieved from IMD 12 for each range to one of ten curve values for each range in order to promote ease of understanding on the part of the user. Processor 30 may maintain look-up tables, or the like, within memory 38, and use the look-up tables to determine a curve value based on a retrieved setpoint value. A greater curve value for a range corresponds to more aggressive rate response within the range.

In some embodiments, user interface 36 may display these curve values and allow a user to make changes to these values via fields of any type, such as a drop-down menus, text boxes, or drop-down menus with text boxes. The embodiment of user interface 36 illustrated in FIGS. 3A–3F displays these curve values and allows a user to make changes to the curve values via slider-bar fields 46 and 48. The positions of the sliders 50 and 52 of each of slider-bar field 46 and 48 is set based on the curve value for that range. For example, as shown in FIG. 3A, the positions both sliders 50 and 52 are set to 6, which are the current curve values for each range corresponding to the setpoint values received from IMD 12 for each range. A user may make changes to these curve values by moving sliders 50 and 52 or clicking on the arrow buttons provided with each slider-bar. The user may make these changes using, for example, a mouse associated with programmer 10.

Processor 30 may also generate a current rate response curve 54 based on the rate limits and setpoint values retrieved from IMD 12, and display current rate response curve 54 via rate response curve window 56. As shown in FIG. 3A, curve window 56 includes a two dimensional coordinate system for plotting sensor indicated rate (on the y-axis) as a function of activity level (on the x-axis). Processor 30 may display curve 54 by drawing a first line for the ADL range with a slope determined based on the currently programmed setpoint value for the ADL range received from IMD 12. The curve value for this range, 6, is indicated on the graph near the first line. Processor 30 may then draw a second line for the exertion range with a slope determined based on the currently programmed setpoint value for the exertion range received from IMD 12. The curve value for this range, 6, is also indicated on the graph, in this case near the second line.

The first line may be drawn from a point on the sensor indicated rate axis at the LR to a point defined by the setpoint value received for the ADL range and the ADLR. Another parameter that processor 30 may receive from IMD 12 is an ADL widthcounts value. Processor 30 may draw a horizontal line at the ADLR from the point corresponding to the setpoint value received for the ADL range and the ADLR from the point defined by the setpoint value received for the ADL range and the ADLR to a point defined by the setpoint value received for the ADL range plus the widthcounts value and the ADLR. The exertion response curve may be drawn from the point defined by the setpoint value received for the ADL range plus the widthcounts value and the ADLR to a point defined by the setpoint value received for the exertion range. Curve window 56 may, as shown in FIG. 3A, include horizontal lines marking the LR, ADLR and USR, which may make curve 54 easier for a user to interpret. By displaying current rate response curve 54 via user interface 36, programmer 10 may make it easier for a user to visualize the current rate response of IMD 12.

As illustrated in FIG. 3A, current rate response curve 54 may be drawn with solid lines. A pending rate response curve, which will be discussed in greater detail below, may be drawn with a different line format, such as a dashed line.

Where IMD 12 is capable of providing for optimization of rate response parameters, processor 30 may receive an indication from IMD 12 that indicates whether IMD 12 is currently operating in an optimization mode. Processor 30 may indicate to a user whether IMD 12 is currently operating in an optimization mode via a field 58, as shown in FIG. 3A. Field 58 may be a drop-down menu, text box, or drop-down menu with a text box, and a user may change the optimization mode of IMD 12 via field 58. For example, a user may select whether rate response optimization is on or off via field 58.

If rate response optimization is on, the user may direct processor 30 to display a target rate histogram window via user interface 36, which will be described in greater detail below, instead of rate response curve window 56. The user may select which window is displayed, via fields of any type provided by processor 30 within user interface 36. For example, the user may select which window is displayed via a drop-down menu, text box, or drop-down menu with text boxes. The embodiment of user interface 36 illustrated in FIGS. 3A–3F includes button fields 60 and 62, by which the user may select which window is displayed. The user may select a window by clicking one of button fields 60 and 62 using a mouse associated with programmer 10. Processor 30 may make the target rate histogram window unavailable to the user when rate optimization is off because target rate histograms are generated based on optimization target values, as will be described in greater detail below. Processor 30 may make this feature of user interface 36 unavailable, by, for example, graying out button field 60 and/or not allowing the user to click on button field 60.

As mentioned above, in addition to currently programmed parameters and optimization target values, processor 30 may retrieve data collected by IMD 12 from IMD 12. Processor 30 may organize and format this data in a form suitable for display, and make this data available for display via user interface 36. For example, IMD 12 may store data indicating the distributions of sensed and paced atrial beats within discrete rate ranges over time. Processor 30 may retrieve this data from IMD 12, generate an atrial rate histogram that illustrates these distributions, and make this atrial rate histogram available for display via user interface 36.

Other data that IMD 12 may collect and processor 30 may retrieve includes data indicating the distributions of sensed and paced ventricular beats within discrete rate ranges over time, data indicating the output of the sensors used to control the rate response of IMD 12 over time, and data indicating the distribution of actual sensor indicated rates within discrete rate ranges over time. Processor 30 may also generate histograms based on these categories of data, and make these histograms available for display via user interface 36.

Processor 30 may provide one or more fields within user interface 36, such as field 64 shown in FIG. 3A, by which a user may direct processor 30 to display such a histogram. Field 64 may be a drop-down menu by which a user may select one of multiple available histograms for display, or a button by which a user may direct processor to display a single histogram, such as an atrial rate histogram. Processor 30 may display these histograms in a different window, or, in some embodiments, may display these histograms alongside a target rate histogram, which will be described in greater detail below.

Figure 3B:
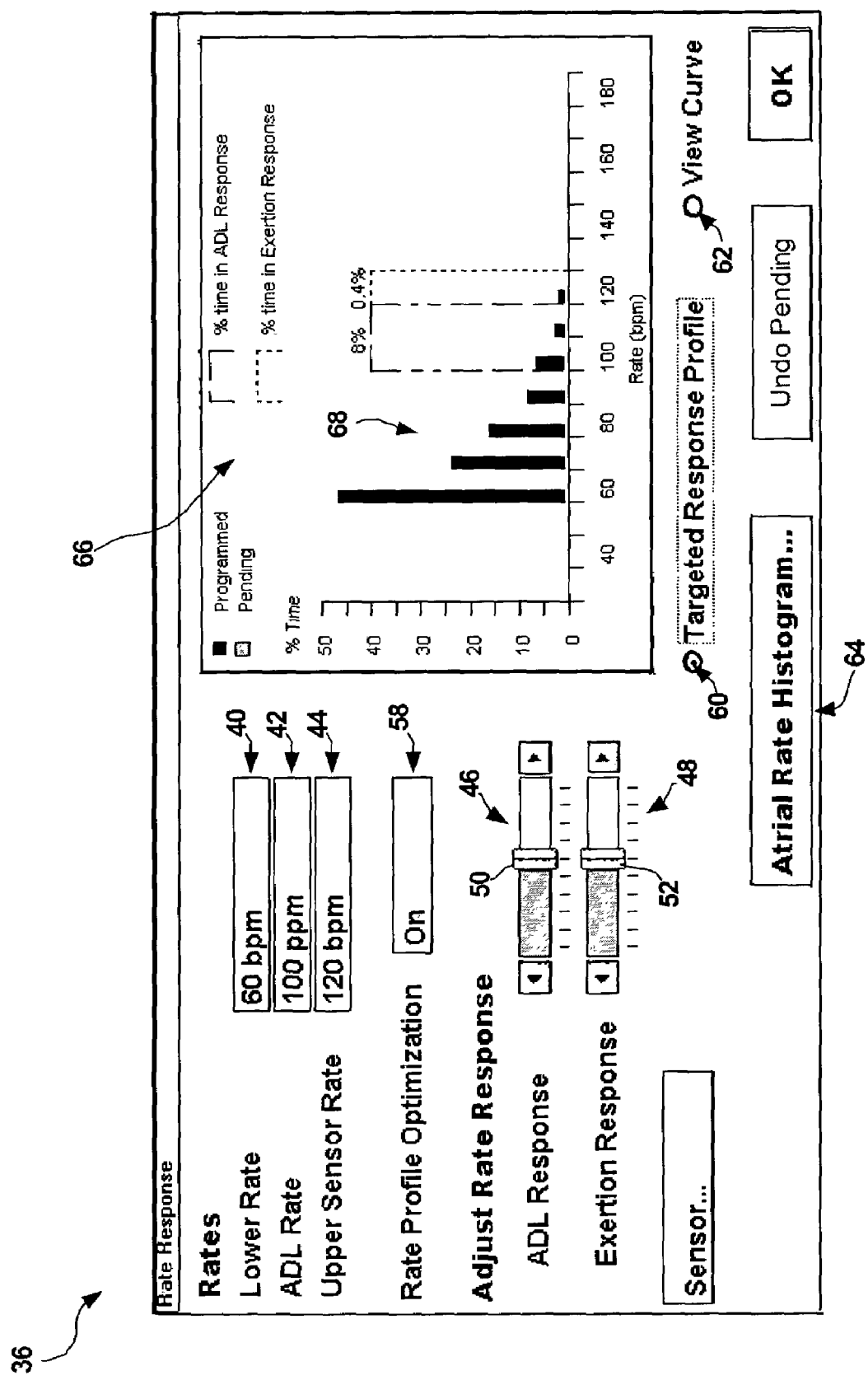

FIG. 3B illustrates user interface 36 when rate response optimization is on, and the user has directed processor 30 to display a target rate histogram window 64 by, for example, clicking button 60 as described above. As discussed above, processor 30 may, when rate response optimization is on, retrieve currently programmed optimization target values from IMD 12. The optimization target values may be percentages of time that IMD 12, through optimization, will cause the sensor indicated rate to be within particular ranges. Processor 30 may retrieve two current optimization target values, the current ADL percentage and current USR percentage, from some dual-slope embodiments of IMD 12, as discussed above.

Figure 3C:
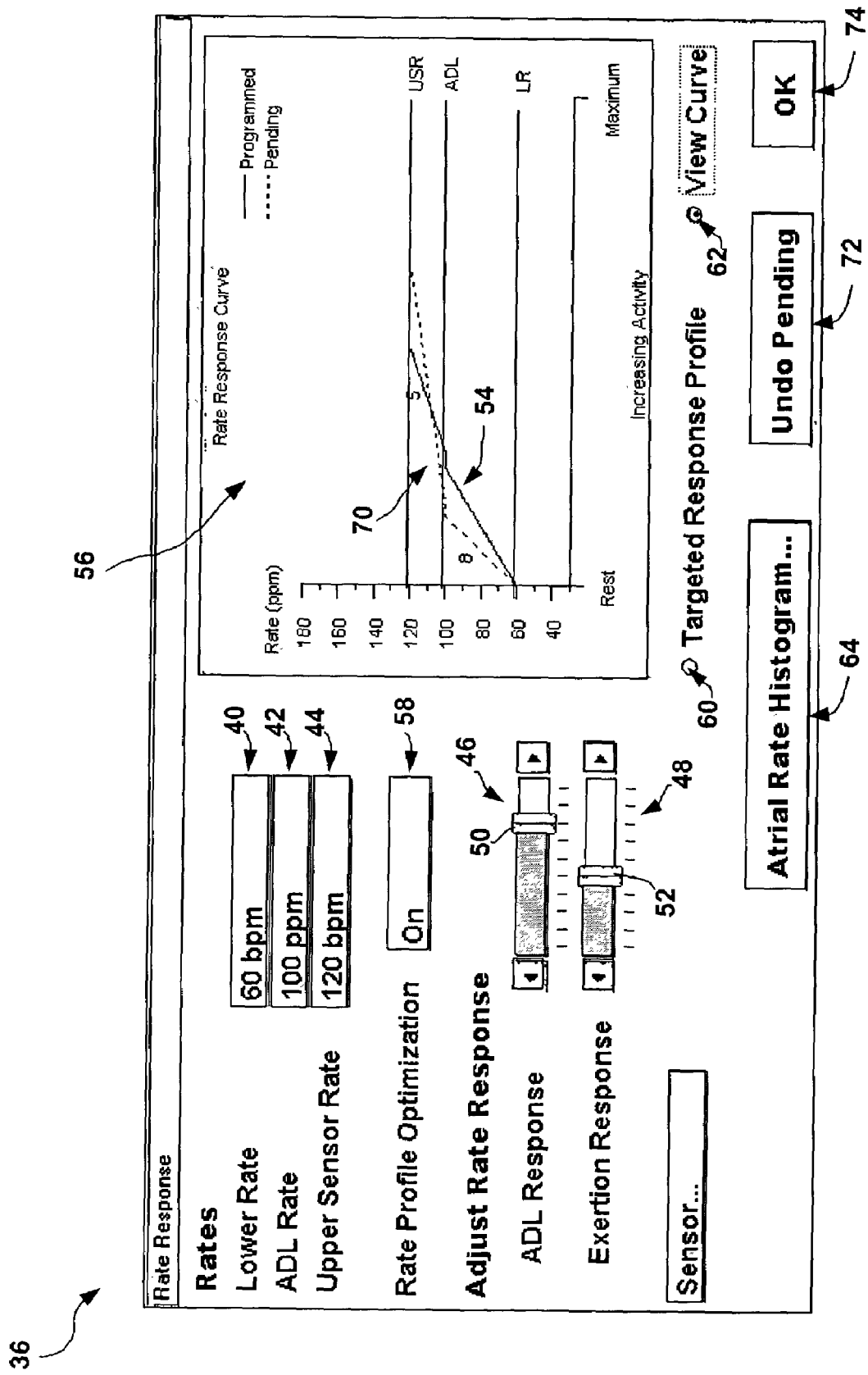

Using the currently programmed target values and rate limits, processor 30 generates a current target rate histogram 68, and displays current target rate histogram 68 within target rate histogram window 64 of user interface 36. Processor 30 may calculate, and current target rate histogram 68 may illustrate estimated percentages of time that IMD 12 will cause the sensor indicated rate to be within a number of discrete rate ranges, or bins, between the LR and USR based on the currently programmed optimization target values. By displaying current target rate histogram via user interface 36, programmer 10 may make it easier for a user to visualize the current rate response of IMD 12, and its effect on patient 14. As shown in FIG. 3C, processor may also display the current ADL percentage and current USR percentage with current target rate histogram 66 in histogram window 64.

As shown in FIG. 3B, target histogram window 66 includes a two dimensional coordinate system for plotting percentage of time (on the y-axis) as a function of sensor indicated rate (on the x-axis). In order to generate current target rate histogram 68, the sensor indicated rate axis is divided into bins. The bins, as shown in FIG. 3B, may be 10 beat-per-minute (b.p.m.) bins. However, bins of any size may be used.

Processor 30 calculates the percentage of time that IMD 12 will cause the sensor indicated rate to be within each bin via optimization based on the optimization target values and the rate limits. Processor 30 determines percentage of time in three rate ranges determined with reference to the rate limits, i.e., the ranges from the LR to the ADLR, from the ADLR to the USR, and at the USR, based on the optimization target values. For example, processor 30 identifies the bin that contains the USR, and calculates the percentage of time in that bin to be the USR percentage, i.e., the percentage of time that IMD 12 will cause the sensor indicated rate to be at the USR. Thus, if, as shown in FIG. 3B, processor 30 retrieves a USR percentage target value of 0.4% from IMD 12, processor 30 will assign 0.4% to the bin, from 120 b.p.m. to 130 b.p.m., that contains the USR, which is 120 b.p.m.

The ADL percentage is the percentage of time that IMD 12 will cause the sensor indicated rate to be within the range from the ADLR to the USR. Processor 30 will distribute the ADL percentage among the bins within this range. Processor 30 may distribute the ADL percentage among the bins by, for example, determining the number of bins within this range and estimating the fraction of the ADL percentage within each bin. Processor 30 may estimate the fraction of the ADL percentage within each bin using a variety of techniques, such as linear interpolation, non-linear, e.g., exponential interpolation, or by referring to a look-up table of percentages generated based on clinical data. Thus, if, as shown in FIG. 3B, processor 30 retrieves an ADL percentage target value of 8% from IMD 12, processor 30 may determine that there are two bins, from 100 b.p.m. to 110 b.p.m. and from 110 b.p.m. to 120 b.p.m., between the ADLR of 100 b.p.m. and the USR of 120 b.p.m., and use any of the above described techniques to assign a fraction of 8% to each of these bins.

Based on the ADL percentage, processor 30 may calculate the percentage of time remaining to be distributed amongst bins within the range from the LR to the ADLR. For example, if, as shown in FIG. 3B, processor 30 retrieves an ADL percentage of 8% from IMD 12, the percentage of time remaining for this range is 100%–8%, or 92%. Processor 30 may distribute this determined percentage of time among the bins within this range by, for example, determining the number of bins within this range and using any of the above-mentioned techniques to estimate the fraction of this below ADLR percentage within each bin.

FIG. 3C illustrates user interface 36 after a user has made a change to a programmed parameter. In particular, as shown in FIG. 3C, the user has manipulated slider-bar fields 46 and 48 to select different rate response curve values for the ADL range and the exertion range. The user has selected a more aggressive rate response within the ADL range than is currently programmed, and a less aggressive response in the exertion range. Slider-bar bar fields 46 and 48, arrows, and buttons indicating "more" and "less" rate response provide an intuitive interface for a user to adjust rate response within these ranges, and are within the scope of this invention. Using such interfaces within user interface 36, a user need not understand the relationship between rate response curve values and setpoint values used by IMD 12 in order to effectively adjust the rate response of IMD 12. Thus user interface 36 may provide a user with a more intuitive to the user for programming or more or less aggressive rate response.

Based on the curve values selected by the user, e.g., the positions of sliders 50 and 52 within slider-bar fields 46 and 48, processor 30 may determine pending setpoint values. Processor 30 may determine pending setpoint values by referring to a look-up table or the like stored within memory 38 that relates curve and setpoint values. Where a curve value selected by the user would lead to combination of setpoint values, i.e., a rate response, that is not capable of being implemented by IMD 12, processor 30 may change the other curve value to achieve an allowed combination of setpoint values. Using the pending setpoint values and the unchanged currently programmed rate limits, processor 30 may generate and display a pending rate response curve 70 within curve window 54 in the manner described above with reference to the generation and display of current rate response curve 54.

Pending rate response curve 70 illustrates what the rate response of IMD 12 would be using the pending parameters selected by the user. Thus, the user is able to evaluate the effect of reprogramming IMD 12 on the rate response of IMD 12 before actually reprogramming IMD 12. As shown in FIG. 3C, pending rate response curve 70 may be displayed via curve window 56 side-by-side with, e.g., at the same time as, current rate response curve 54. By displaying current rate response curve 54 and pending rate response curve 70 side-by-side, programmer 10 may allow the user to more easily visualize the effect of the changes made to rate response parameters on the rate response of IMD 12, making programming IMD 12 more intuitive for the user. Moreover, the user may evaluate the effect of these changes before submitting them to IMD 12, i.e. without reprogramming IMD 12 with the changed parameters, and without an exercise test. Processor 30 may, as shown in FIG. 3C, display current rate response curve 54 and pending rate response curve 70 with different line formats so that they may be more easily distinguished from each other.

Processor 30 may provide fields 72 and 74 within user interface 36 that allow a user to undo changes made to rate response parameters and accept changes made to rate response parameters respectively. Fields 72 and 74 may, as shown in FIG. 3C, be button fields, and a user may use a mouse to click either of fields 72 and 74. If the user clicks undo field 72, processor 30 may remove pending rate response curve 70 from curve window 56, and return sliders 50 and 52 to their original position. Processor may store currently programmed parameters, including the current programmed setpoint values and determined curve values, and pending parameters, including pending setpoint values and curve values, within memory 38 in order to facilitate this process. If the user clicks accept field 74, processor 30 may reprogram IMD 12 with the pending parameters.

Figure 3D:
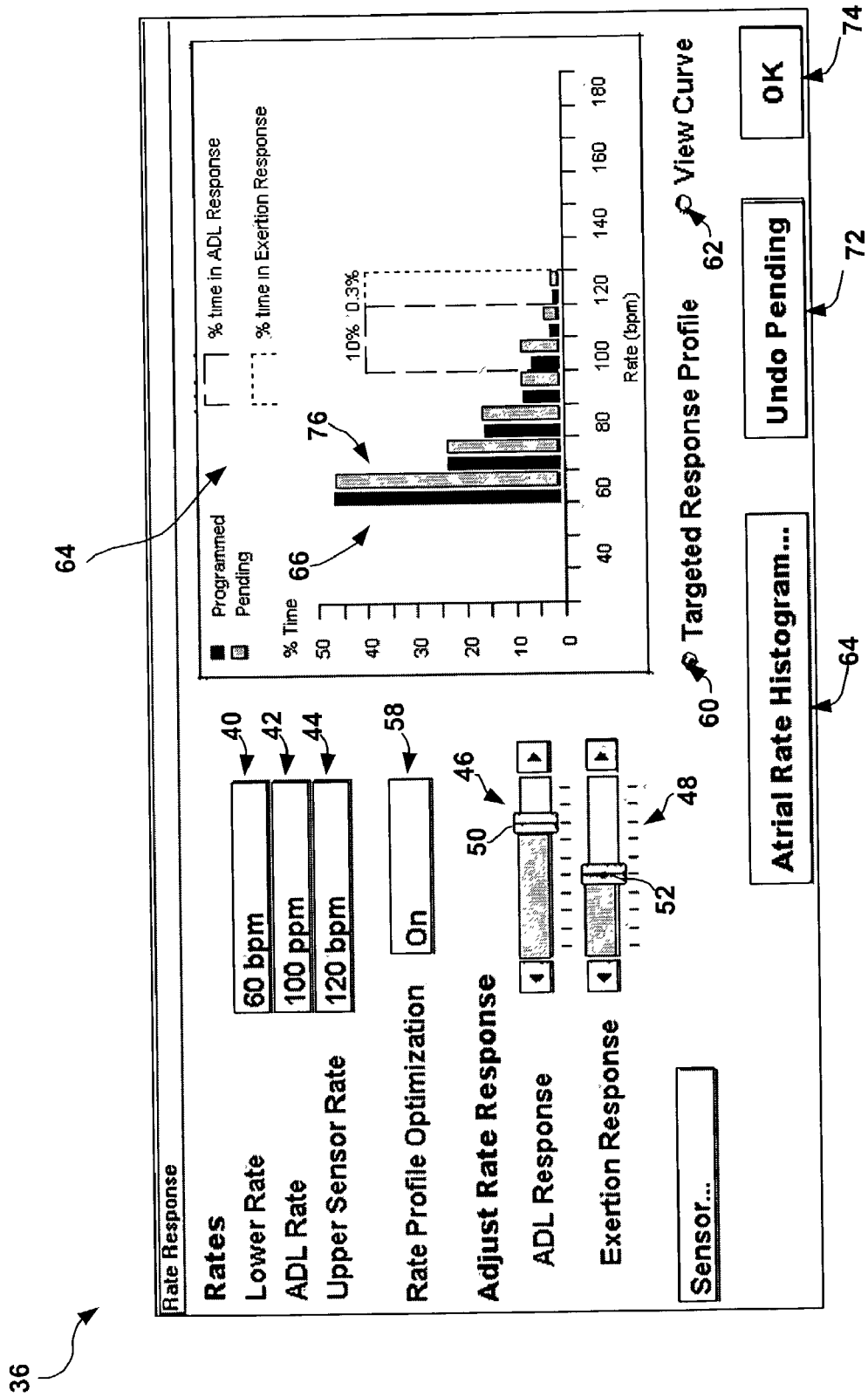

FIG. 3D illustrates user interface 36 with target histogram window 64 displayed after a user has manipulated slider-bar fields 46 and 48 to select different rate response curve values for the ADL range and the exertion range, as described above. The user may have selected target histogram window 64 as described above after manipulating slider-bar fields 46 and 48 with curve window 56 displayed, or user may have manipulated slider-bar fields 46 and 48 with target histogram window displayed.

In either situation, when processor 30 receives a change or adjustment made by a user to either the ADL range or exertion range curve value, processor 30 may make a corresponding change or adjustment to the appropriate optimization target value, i.e., either the ADL percentage or the USR percentage. In other words, the user may make changes to the optimization target values via the ADL range and exertion range fields 46 and 48. Processor 30 may refer to a look-up table or the like in stored in memory 38 to determine the pending optimization target value based on the input made by the user via fields 46 and 48. The look-up table may include a number of possible values for the optimization targets, including the currently programmed target values.

If, for example, the user increments or decrements slider 50 by one position processor 30 may select the next greater or lesser ADL percentage value within a look-up table for ADL percentage values relative to the currently programmed ADL percentage value. If the next greater or lesser target value is not available, i.e., if the target is already at the highest or lowest possible value, processor 30 will continue to make changes to the curve value without changing the target value. In the example shown in FIG. 3D, the user has incremented slider 50 of ADL range field 46 by two curve values, from the original curve value of 6 to a pending curve value of 8, and decremented slider 52 of exertion range field 48 by one curve value, from an original curve value of 6 to a pending curve value of 5. Processor 30 has selected a pending ADL percentage of 10%, which may have been two entries within a look-up table for ADL percentages greater than the current programmed ADL percentage of 8%, and a pending USR percentage of 0.3%, which may have been one entry within a look-up table for USR percentages less than the current programmed USR percentage of 0.4%.

When the user intends to change an optimization target value, the corresponding change in the rate response curve value, and thus the setpoint value, will advantageously bring the setpoint value closer to the value that IMD 12 would arrive at through optimization based on the changed optimization target values at the time of programming. Thus, the association of changes made to target values with changes to curve values in this manner will advantageously allow the patient to more quickly feel the effect of the changes when IMD 12 is reprogrammed with the changed setpoint values and optimization values. Further, this association will allow the user to more quickly evaluate whether the changes made are effective.

Using the pending target values and the unchanged rate limits, processor 30 may generate and display a pending target rate histogram 76 in the manner described above with reference to the generation of the current target rate histogram 66. Pending target rate histogram 76 illustrates estimated percentages of time that IMD 12 would cause the sensor indicated rate to be within a number of discrete rate ranges using the pending optimization target values. Thus, the user is able to evaluate the effect of reprogramming IMD 12 on the rate response of IMD 12 before actually reprogramming IMD 12. The user may reprogram IMD 12 or undo the pending changes via fields 74 and 72 of user interface 36, as described above.

As shown in FIG. 3D, pending target rate histogram 76 may be displayed via target histogram window 64 side-by-side with, e.g., at the same time as, current target rate histogram 66. By displaying current target rate histogram 66 and pending target rate histogram 76 side-by-side, programmer 10 may allow the user to more easily visualize the effect of the changes made to optimization target values on the rate response of IMD 12, making programming IMD 12 more intuitive for the user. Moreover, the user may evaluate the effect of these changes before submitting them to IMD 12, i.e. without reprogramming IMD 12 with the changed parameters, and without an exercise test. Processor 30 may, as shown in FIG. 3D, display current target rate histogram 66 and pending target rate histogram 86 with different shading so that they may be more easily distinguished from each other.

Figure 3E:
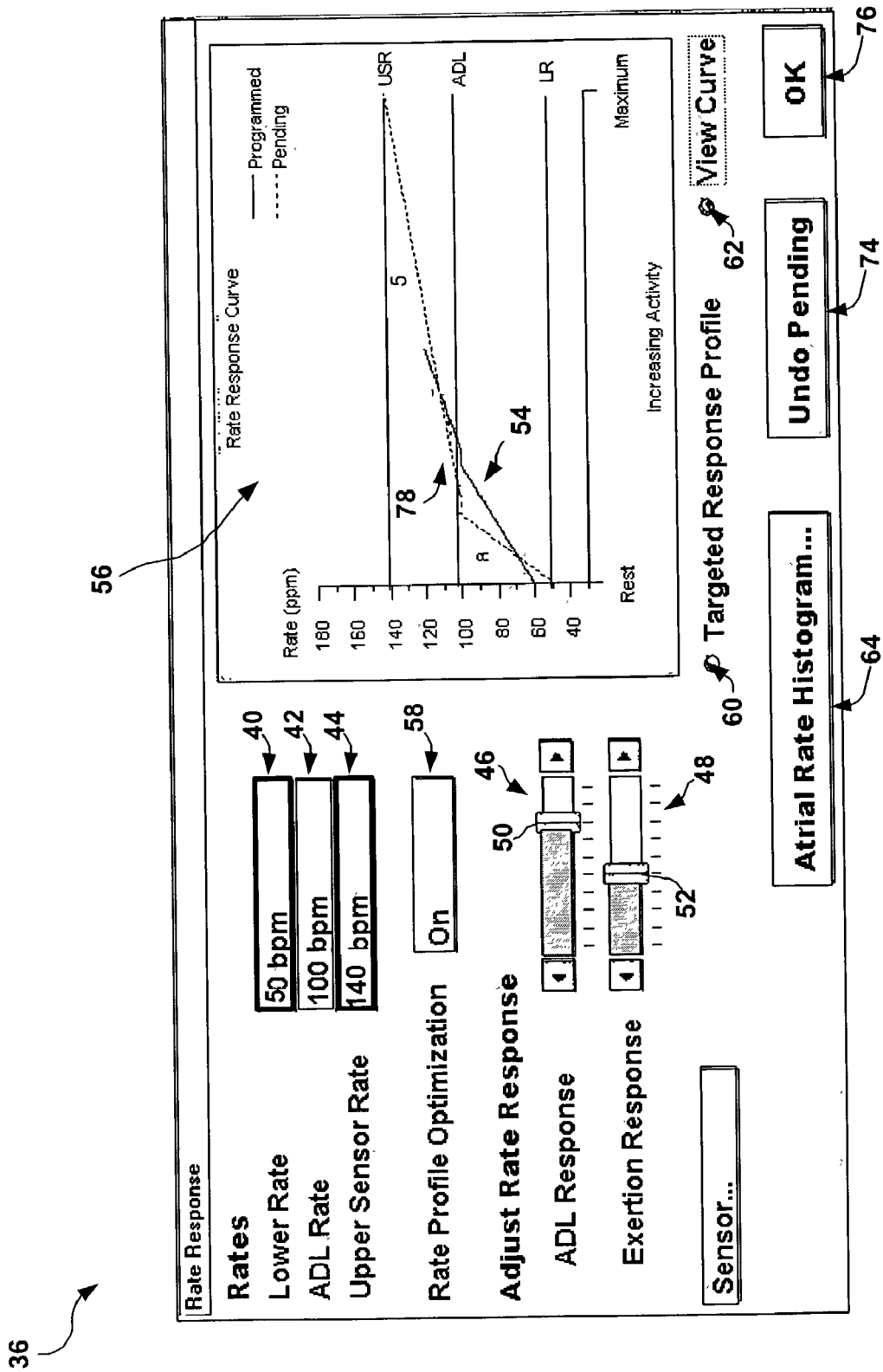
Figure 3F:
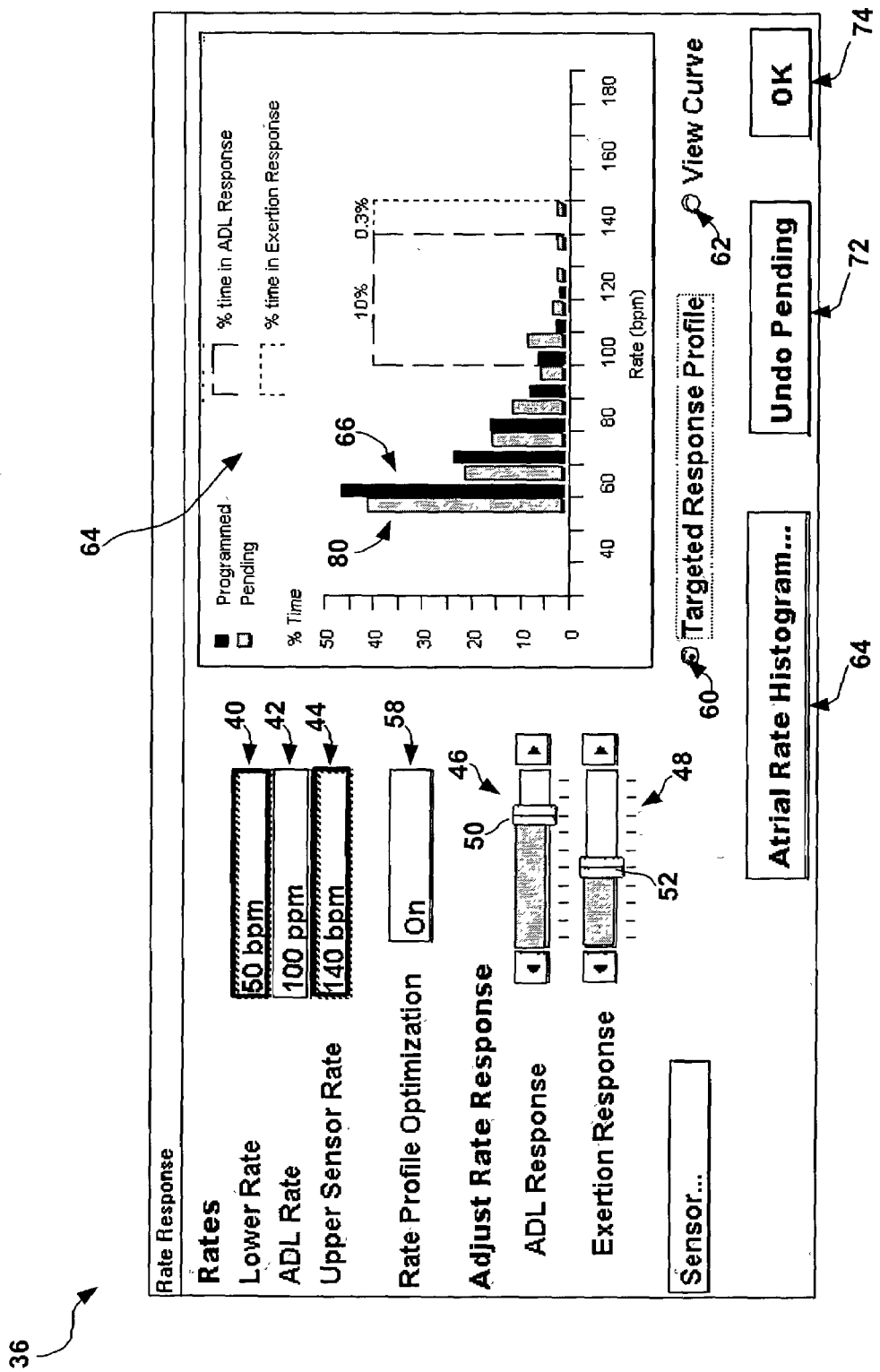

FIGS. 3E and 3F illustrate user interface 36 with rate response curve window 56 and target rate histogram window 66 displayed, respectively, after a user has modified additional programmed parameters, such as the rate limits within fields 40–44. Although FIGS. 3E and 3F illustrate these modifications to rate limits in addition to modifications to curve values and optimization target values made via ADL range and exertion range fields 46 and 48, it is to be understood that these modifications to rate limits may be made in the absence of other modifications to the programming of IMD 12. Further, although FIGS. 3E and 3F illustrate these modifications only to rate limits within fields 40 and 44, it is to be understood that the rate limit of field 42 may also be modified. In other words, a user may modify any one of or combination of currently programmed parameters, current rate response curve values, or currently programmed optimization target values displayed via user interface 36 consistent with the invention.

In the example illustrated by FIGS. 3E and 3F, the user has modified the LR within field 40 from the currently programmed value of 60 b.p.m. to a pending value of 50 b.p.m., and the USR within field 44 from the currently programmed value of 120 b.p.m. to a pending value of 140 b.p.m. As shown in FIGS. 3E and 3F, fields 40 and 44 may be shaded or the like to indicate that they are currently displaying pending values. As shown in FIG. 3E, based on the pending rate limits and the pending setpoint values that were discussed above with reference to FIG. 3C, processor 30 may generate and display a pending rate response curve 78 in the manner discussed above. Further, as shown in FIG. 3F, based on the pending rate limits and the pending optimization target values that were discussed above with reference to FIG. 3D, processor 30 may generate and display a pending target rate histogram 80 in the manner discussed above. Display of the pending curve 78 and histogram 80, and display of the pending curve 78 and histogram 80 alongside a current curve 54 and histogram 66 respectively may provide the advantages discussed above. Further, the user may reprogram IMD 12 or undo the pending changes via fields 74 and 72 of user interface 36, as described above.

Figure 4:
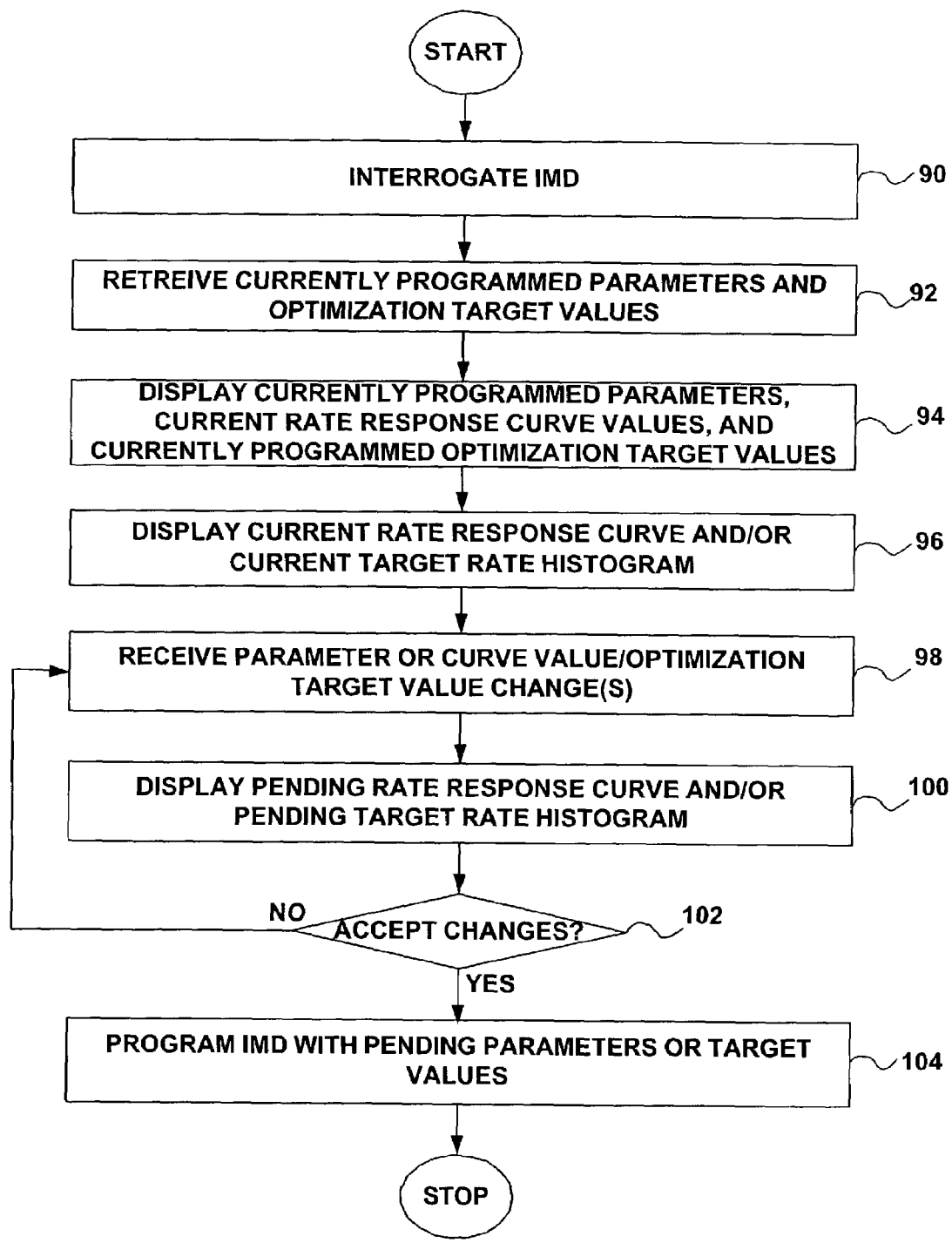
FIG. 4 is a flow diagram illustrating an exemplary method for programming a rate responsive implantable medical device via a programmer that includes user interface.

FIG. 4 is a flow diagram illustrating an exemplary method for programming a rate responsive IMD, such as IMD 12, via programmer 10 and user interface 36. Processor 30 of programmer 10 interrogates IMD 12 (90) to retrieve currently programmed parameters (92). Where IMD 12 is in an optimization mode, processor 30 may also retrieve currently programmed optimization target values. Processor 30 may also retrieve data collected by IMD 12 and stored within a memory of IMD 12, as described above. Processor 30 may interrogate IMD 12 via transceiver 32 and antenna 34, which may correspond to a programming head of programmer 10 placed over IMD 12.

Processor 30 displays the at least some of the currently programmed parameters to a user via user interface 36 (94). The currently programmed parameters displayed via user interface 36 may include rate limits, such as the LR, ADLR and USR, and may also include acceleration and decay constants. The currently programmed parameters may be displayed via fields of user interface 36, such as fields 40–44. The currently programmed parameters may also include one or more currently programmed setpoint values described above, and processor 30 may determine and display current curve values, such as an ADL range curve value and an exertion curve value, based on the setpoint values. The curve values may be displayed via fields of user interface 36 such as slider-bar fields 46 and 48. Where IMD 12 is in an optimization mode, processor 30 may also display currently programmed optimization target values.

Processor 30 generates a current rate response curve 54 based on the currently programmed parameters, e.g., the rate limits and setpoint values retrieved from IMD 12, and display current rate response curve 54 to a user via user interface 36 (96). Where IMD 12 is in an optimization mode, processor 30 may generate a current target rate histogram 66 based on the rate limits and the currently programmed optimization target values, and display current target rate histogram 66 via user interface 36, as discussed above. The curve 54 and histogram 66 may be presented via different windows provided by user interface 36, and a user may select which window processor 30 will display via fields within user interface 36, such as button fields 70 and 72, as discussed above. By displaying current curve 54 and current histogram 66, programmer 10 enables a user to better visualize the effect of the current programming of IMD 12 on the rate response of IMD 12.

The user may make changes to the currently programmed rate response parameters, current curve values, or currently programmed optimization target values displayed via user interface 36 by interacting with fields of user interface 36 that contain these values, and processor 30 may display these changes (98). Processor 30 may provide fields within user interface 36, such as slider-bar fields 46 and 48, that allow the user to change both a curve value and a target value by a single action, as described above. The use of slider-bar fields 46 and 48, or similar fields, allows the user to intuitively increase or decrease the aggressiveness of the rate response of IMD 12 within a range. The changing of a curve value when changing a target value brings the pending parameters closer to the values that IMD 12 would arrive at through optimization. When IMD 12 is programmed with these parameters patient 14 may more quickly feel the benefit of the changes, the user may more quickly evaluate the effect of these changes.

Processor 30 generates and displays a pending rate response curve 70,78 via user interface 36 based on the pending parameters and the unchanged currently programmed parameters, and may, if IMD 12 is in an optimization mode, generate and display a pending target rate histogram 76,80 via user interface 36 based on the pending parameters or target values, and the unchanged currently programmed parameters or target values (100). Processor 30 may display current and pending curves and histograms via user interface side-by-side, allowing the user to more easily visualize the effect of the changes made programmed parameters or optimization target values on the rate response of IMD 12, making programming IMD 12 more intuitive for the user, and allowing the user to evaluate the effect of these changes before reprogramming IMD 12, and without an exercise test.

If the user accepts the changes made via user interface 36 (102), processor 30 may reprogram IMD 12 with the pending parameters or target values replacing currently programmed parameters or optimization target values (104). If the user does not accept the pending parameters (102), processor 30 may reset user interface 36 with currently programmed parameters, and/or wait to receive more changes made by the user via user interface 36 (98). Processor 30 may provide fields within user interface 36, such as button fields 70 and 72, that allow a user to accept or undo pending parameters or target values.

Figure 5:
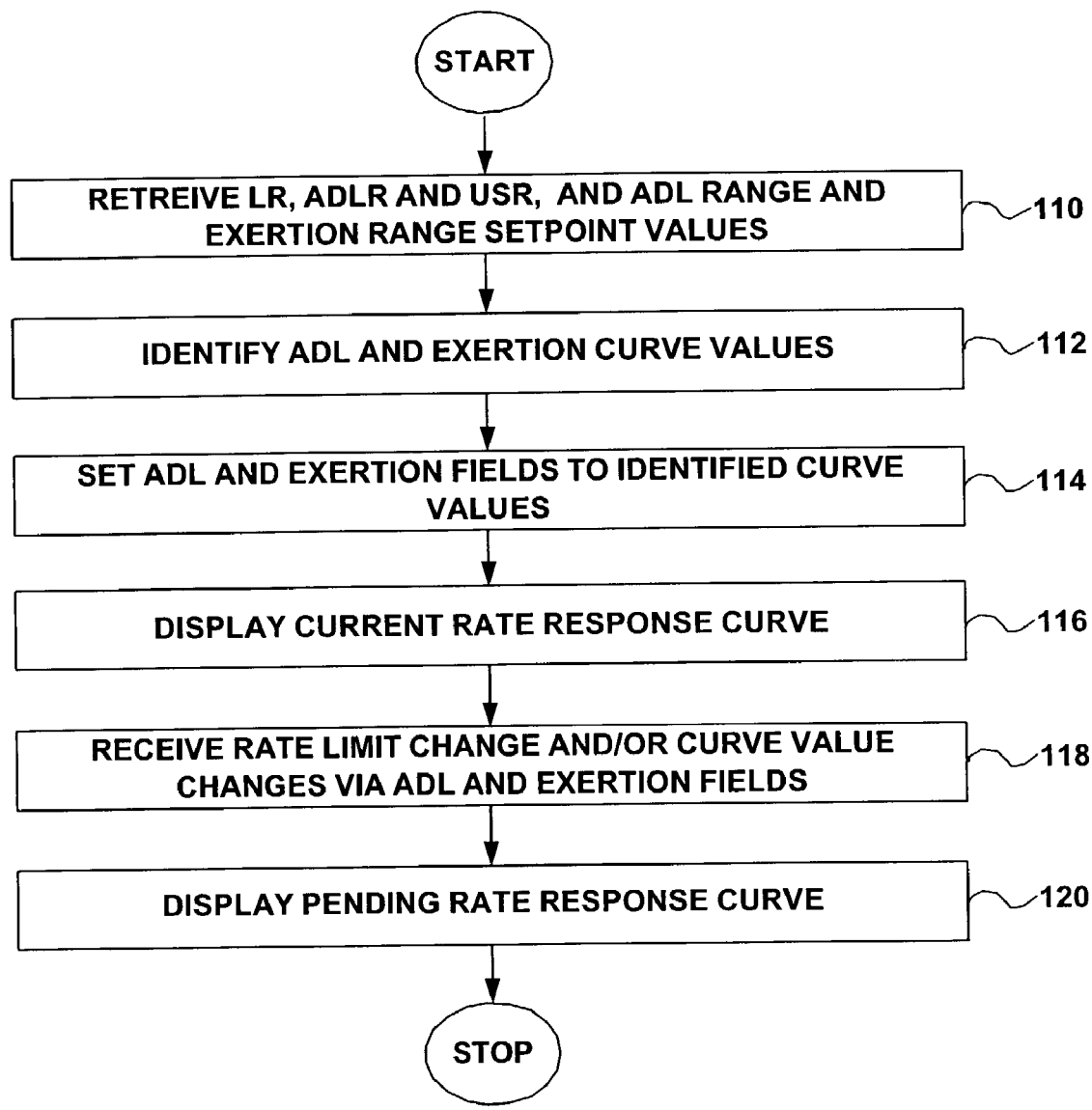
FIG. 5 is a flow diagram illustrating an exemplary method for generating current and pending rate response curves.

FIG. 5 is a flow diagram illustrating an exemplary method for providing current and pending rate response curves. The currently programmed parameters retrieved from IMD 12 may include current rate limits, such as the LR, ADLR and USR, and current setpoint values, such as an ADL and an exertion setpoint value (110). Processor 30 identifies current ADL and exertion curve values based on the currently programmed setpoint values (112). Processor 30 may refer to look-up tables or the like within memory 38 to determine a curve value based on a retrieved setpoint value. Processor 30 then sets ADL range and exertion range fields 46 and 48 within user interface 36 to the current ADL and exertion curve values (114). Fields 46 and 48 may be slider-bar fields, and may include sliders 50 and 52 positioned according to the current curve values.

Processor 30 also generates and displays a current rate response curve 54 based on the rate limits and setpoint values retrieved from IMD 12 (116), receives parameter changes (118), and displays a pending rate response curve based on the pending parameters (120). Where the user makes a change to a curve value by manipulating one of curve value fields 46 and 48, processor 30 will determine a pending setpoint value based on the new curve value so that the pending rate response curve may be generated. Processor 30 may refer to look-up tables or the like within memory 38 to determine a setpoint value based on the new curve value. Moreover, the processor 30 will use the determined pending setpoint value to reprogram IMD 12 if the user accepts the changes made.

Figure 6:
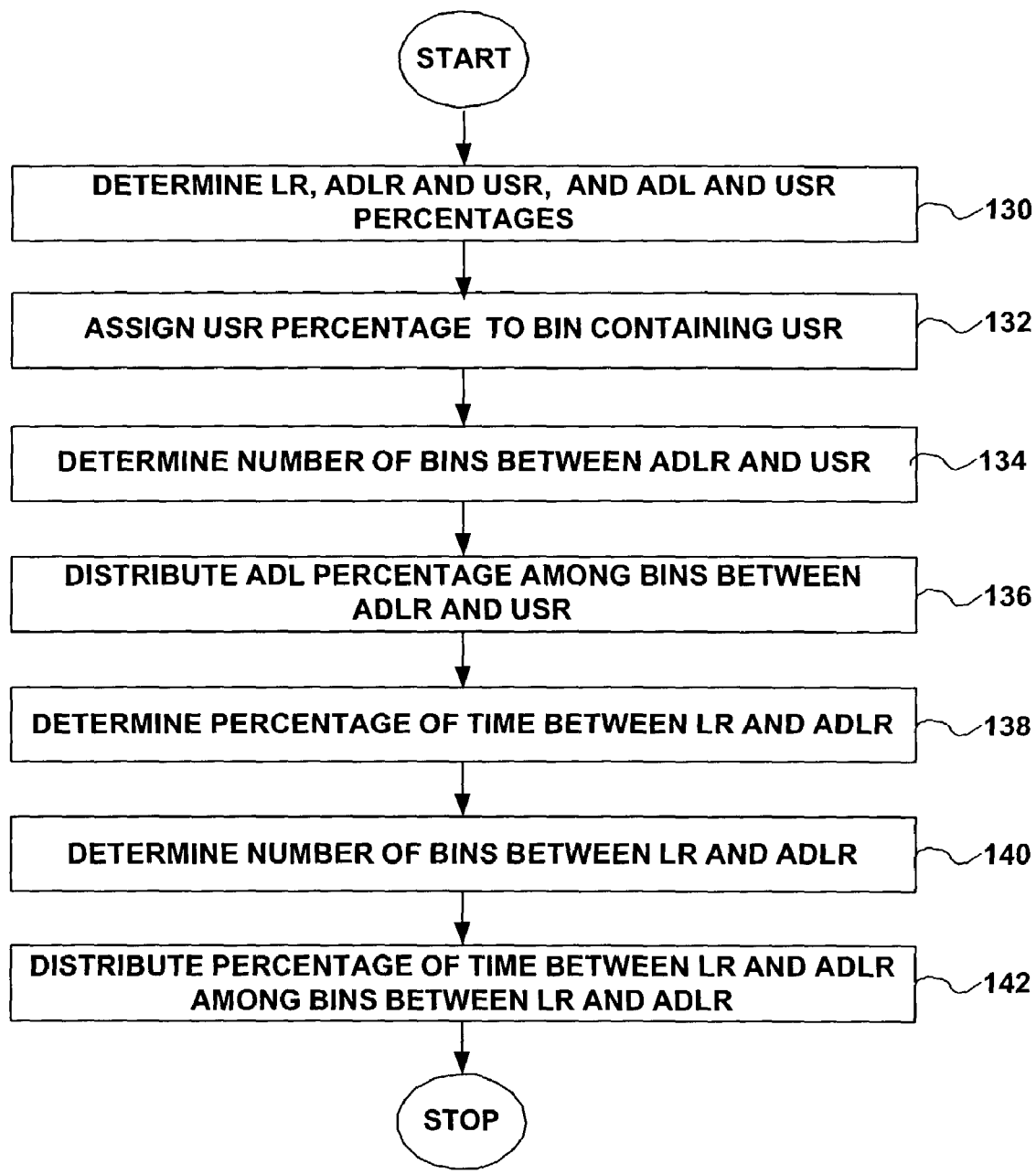
FIG. 6 is a flow diagram illustrating an exemplary method for generating a current or pending target rate histogram.

FIG. 6 is a flow diagram illustrating an exemplary method for generating a current or pending target rate histogram. Processor 30 determines current or pending programmed rate limits, such as the LR, ADLR and USR, and current or pending programmed optimization target values, such as the ADL percentage and the USR percentage (130). Processor 30 may retrieve current programmed rate limits and currently programmed target values from IMD 12 to generate a current target rate histogram, and may receive pending rate limits and/or target values from a user via user interface 36 to generate a pending target rate histogram based on the pending limits or values, and the unchanged limits or values. Processor 30 generates a current or pending target histogram by estimating percentages of time that IMD 12 will cause the sensor indicated rate to be within a number of discrete rate ranges, or bins, between the LR and the USR via optimization. Processor 30 estimates these percentages based on optimization target values, such as the ADL percentage and USR percentage, that are percentages of time that IMD 12 will cause the sensor indicated rate to be within subsets of the range from the LR to the USR via optimizations. The bins may be 10 b.p.m bins.

Processor 30 assigns the USR percentage, which is the percentage of time IMD 12 will cause the sensor indicated rate to be at the USR, to the bin containing the USR (132). Processor 30 also determines the number of bins between the ADLR and the USR (134), and distributes the ADL percentage, which is the percentage of time IMD 12 will cause the sensor indicated rate to be between the ADLR and the USR via optimization, among these bins, by, for example, using linear or non-linear interpolation, or by referring to a look-up table of percentages generated based on clinical data, to determine the fraction of the ADL percentage to assign to each bin (136). Processor 30 also determines the percentage of time that IMD 12 will cause the sensor indicated rate to be within the remainder of the rate range between the LR and the USR, i.e., the rate range between the LR and the ADLR by subtracting the ADL percentage from 100% (138), determines the number of bins within this range (140), and distributes the determined percentage of time among the determined bins by, for example, using the above-mentioned techniques to determine the fraction of the determined percentage to assign to each bin (142).

Figure 7:
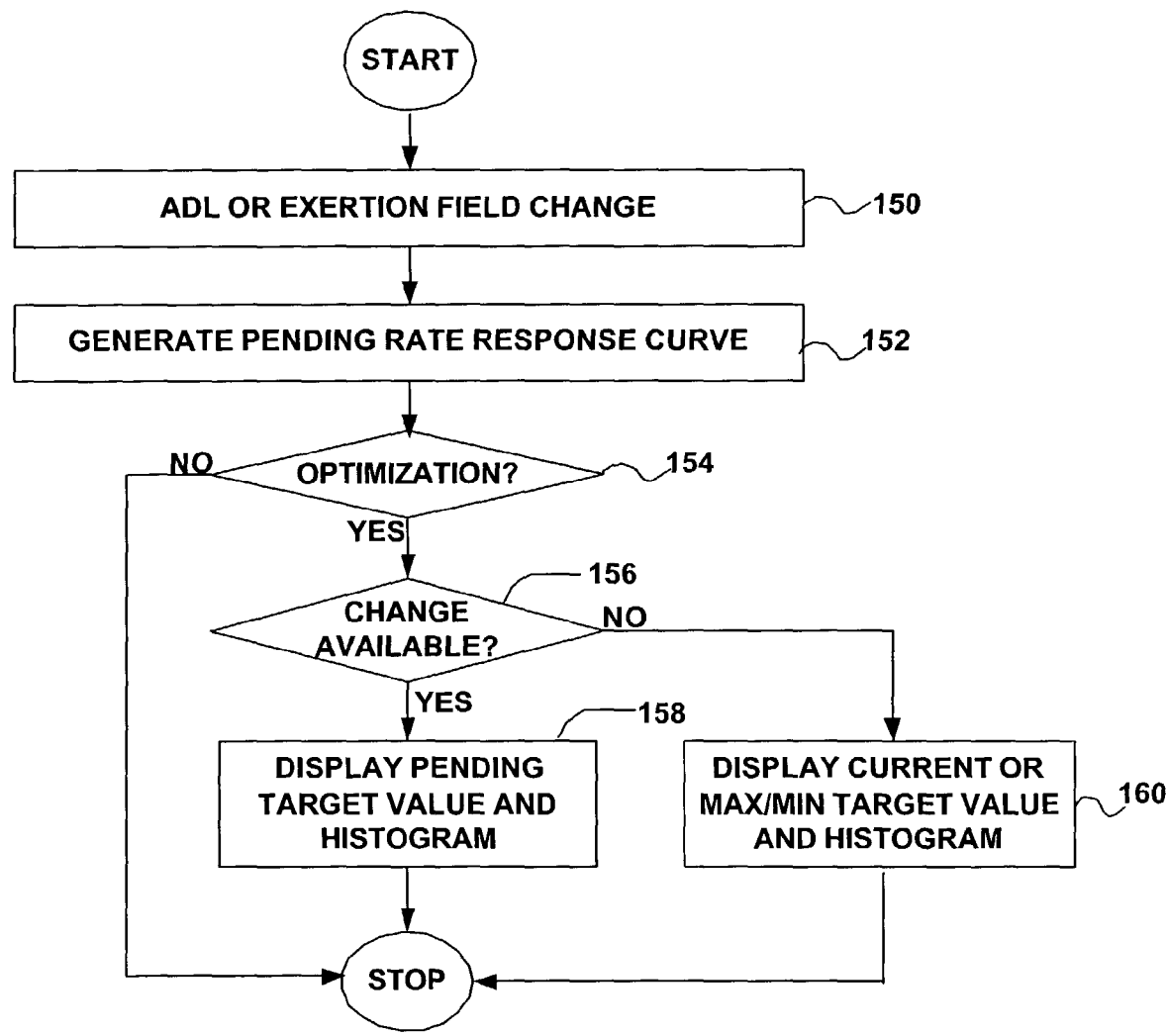
FIG. 7 is a flow diagram illustrating an exemplary method for adjusting rate response curve values and optimization target values based on user interaction with rate response curve value fields.

FIG. 7 is a flow diagram illustrating an exemplary method for adjusting rate response curve values and optimization target values based on user interaction with rate response curve value fields 46 and 48 of user interface 36. Fields 46 and 48 may be slider-bar fields, as described above. When processor 30 receives a change or adjustment made by a user to either the ADL range or exertion range curve value fields 46 and 48 (150), processor 30 will generate a pending rate response curve based on the new curve value (152). The user may change the curve value by moving a slider 50 or 52 of field 46 or 48. Processor 30 may generate the pending rate response curve by determining a corresponding pending setpoint value and generating the curve based on the pending setpoint value, as described above.

When the user changes the curve value, if IMD 12 is in an optimization mode (154), processor 30 may determine whether a corresponding change to the appropriate optimization target value, i.e., either the ADL percentage or the USR percentage, is available (156). Processor 30 may refer to a look-up table or the like in stored in memory 38 of IMD 12 to determine the pending optimization target value based on the input made by the user via fields 46 and 48, e.g., by traversing the look-up table from the currently programmed target value based on the number of curve values or slider positions of the change made by the user, as described above. If a target value within the table corresponding to the user input is available, processor 30 will display the pending target value and generate a pending target rate histogram based on the pending target value (158). If the input made by the user exceeds the upper or lower limit of the look-up table, processor 30 may not make the change and display the current target value and current target rate histogram, or may display as the pending target value the maximum or minimum target value and display the pending target rate histogram based on the maximum or minimum target value (160).

As described above, associating changes in optimization target values with changes in rate response curve values, and thus the setpoint values, will advantageously bring the setpoint values closer to the values that IMD 12 would arrive at through optimization based on the changed optimization target values at the time of programming. Thus, the association of changes made to target values with changes to curve values in this manner will advantageously allow the patient to more quickly feel the effect of the changes when IMD 12 is reprogrammed with the changed setpoint values and optimization values. Further, this association will allow the user to more quickly evaluate whether the changes made are effective.

Various embodiments of the invention have been described. It is to be understood, however, that in light of this disclosure, other embodiments will become apparent to those skilled in the art. For example, programmer 10 may be embodied in any type of computing device, such as a handheld computer, laptop computer, desktop computer, workstation, or the like. In some embodiments, programmer 10 may interact with IMD 12 remotely via a computer network.

Although optimization target values have been described herein as percentages of time, the invention is not so limited. Optimization target values may be expressed as times per day, week, month, or the like for the sensor indicated rate to be within a particular rate range, and IMD 12 may optimize the rate response to achieve these targets. A target rate histogram generated based on such a optimization target value would estimate an amount of time per day, week, month, or the like that IMD 12 would cause the sensor indicated rate to be within each bin. Accordingly, these and other embodiments are within the scope of the following claims.

What is claimed is:

1. A method of programming a rate response field for an implantable medical device without subjecting a patient to an exercise test or the like, comprising:
   receiving currently programmed rate response parameters and at least one currently programmed optimization target value from an implantable medical device;
   displaying the currently programmed parameters and at least one target value via a user interface;
   generating a current rate response curve which represents sensor indicated rate as a function of activity level based on the currently programmed parameters, and a current target rate histogram which represents an estimate of percentage of time as a function of sensor indicated rate based solely upon the currently programmed parameters and at least one target value without subjecting a patient receiving therapy from the implantable medical device to either an exercise test or a predetermined regimen of exertion and without first reprogramming the implantable medical device; and
   displaying both the current rate response curve and the current target rate histogram via the user interface.

2. The method of claim 1, wherein receiving currently programmed rate response parameters comprises receiving currently programmed rate limits and setpoint values, and displaying at least some of the currently programmed parameters comprises:
   displaying the currently programmed rate limits;
   determining current curve values based on the currently programmed setpoint values; and
   displaying the current curve values.

3. The method of claim 2, wherein generating a current rate response curve comprises generating a current rate response curve based on the currently programmed rate limits and setpoint values.

4. The method of claim 2, wherein determining the current curve values comprises identifying the current curve values in a look-up table based on the currently programmed setpoint values.

5. The method of claim 1, wherein receiving at least one currently programmed optimization target value comprises receiving at least one target percentage of time for a sensor indicated rate to be within a range of rates.

6. The method of claim 5, wherein generating a current target rate histogram comprises estimating the percentage of time that the implantable medical device causes the sensor indicated rate to be within a number of rate range bins based on the at least one currently programmed optimization target value.

7. The method of claim 1, further comprising:
   receiving a change made by a user to at least one of the currently programmed parameters via a user interface;
   generating a pending rate response curve and a pending target rate histogram based on the change; and
   displaying the pending rate response curve and the pending target rate histogram via the user interface.

8. The method of claim 7, wherein displaying the pending rate response curve and the pending target rate histogram comprises:
   displaying the current rate response curve and the pending rate response curve at the same time within a first window of the user interface; and
   displaying the current target rate histogram and the pending target rate histogram at the same time within a second window of the user interface.

9. The method of claim 7, further comprising reprogramming the implantable medical device based on the at least one changed parameter.

10. The method of claim 7, wherein receiving currently programmed rate response parameters comprises receiving currently programmed setpoint values, receiving a change made by a user to at least one of the currently programmed parameters comprises:
  determining current curve values based on the currently programmed setpoint values;
  displaying the current curve values via the user interface;
  receiving a change made by a user to at least one current curve value via the user interface; and
  determining at least one pending setpoint value based on the change, and generating a pending rate response curve comprises generating a pending rate response curve based on the at least one pending setpoint value.

11. The method of claim 10, further comprising determining at least one pending optimization target value based on the change to at least one current curve value, wherein generating a pending target rate histogram comprises generating a pending target rate histogram based on the at least one pending optimization target value.

12. The method of claim 11, wherein determining a pending optimization target value based on a change to a current curve value comprises identifying a pending optimization target value within a lookup table based on the magnitude of the change of the curve value.

13. The method of claim 1, further comprising:
  receiving data from the implantable medical device; and
  displaying at least one of an atrial rate histogram, ventricular rate histogram, and actual sensor indicated rate histogram via the user interface based on the data.

14. The method of claim 13, wherein displaying at least one of an atrial rate histogram, ventricular rate histogram, and actual sensor indicated rate histogram comprises displaying at least one of an atrial rate histogram, ventricular rate histogram, and actual sensor indicated rate histogram within the same window and at the same time as at least one of the current target rate histogram and a pending target rate histogram.

15. A computer-readable medium comprising instruction that cause a processor to:
  receive currently programmed rate response parameters and at least one currently programmed optimization target value from an implantable medical device;
  display the currently programmed parameters and at least one target value via a user interface;
  generate a current rate response curve which represents sensor indicated rate as a function of activity level based on the currently programmed parameters, and a current target rate histogram which represents an estimate of percentage of time as a function of sensor indicated rate based solely upon the currently programmed parameters and at least one target value and without reference to any signals derived from either a prescribed exercise test or regimen of exertion by a patient and without first reprogramming the implantable medical device; and
  display the curve and the histogram via the user interface.

16. The computer-readable medium of claim 15, wherein the instructions that cause a processor to receive currently programmed rate response parameters comprise instructions that cause a processor to receive currently programmed rate limits and setpoint values, and the instructions that cause a processor to display at least some of the currently programmed parameters comprise instructions that cause a processor to:
  display the currently programmed rate limits;
  determine current curve values based on the currently programmed setpoint values; and
  display the current curve values.

17. The computer-readable medium of claim 16, wherein the instructions that cause a processor to generate a current rate response curve comprise instructions that cause a processor to generate a current rate response curve based on the currently programmed rate limits and setpoint values.

18. The computer-readable medium of claim 16, wherein the instructions that cause a processor to determine the current curve values comprise instructions that cause a processor to identify the current curve values in a look-up table based on the currently programmed setpoint values.

19. The computer-readable medium of claim 15, wherein the instructions that cause a processor to receive at least one currently programmed optimization target value comprise instructions that cause a processor to receive at least one target percentage of time for a sensor indicated rate to be within a range of rates.

20. The computer-readable medium of claim 19, wherein the instructions that cause a processor to generate a current target rate histogram comprise instructions that cause a processor to estimate the percentage of time that the implantable medical device causes the sensor indicated rate to be within a number of rate range bins based on the at least one currently programmed optimization target value.

21. The computer-readable medium of claim 15, further comprising instructions that cause a processor to:
  receive a change made by a user to at least one of the currently programmed parameters via a user interface;
  generate a pending rate response curve and a pending target rate histogram based on the change; and
  display the pending rate response curve and the pending target rate histogram via the user interface.

22. The computer-readable medium of claim 21, wherein the instructions that cause a processor to display the pending rate response curve and the pending target rate histogram comprise instructions that cause a processor to:
  display the current rate response curve and the pending rate response curve at the same time within a first window of the user interface; and
  display the current target rate histogram and the pending target rate histogram at the same time within a second window of the user interface.

23. The computer-readable medium of claim 21, further comprising instructions that cause the processor to reprogram the implantable medical device based on the at least one changed parameter.

24. The computer-readable medium of claim 21, wherein the instructions that cause a processor to receive currently programmed rate response parameters comprise instructions that cause a processor to receive currently programmed setpoint values, the instructions that cause a processor to receive a change made by a user to at least one of the currently programmed parameters comprise instructions that cause a processor to:
  determine current curve values based on the currently programmed setpoint values;
  display the current curve values via the user interface;
  receive a change made by a user to at least one current curve value via the user interface; and
  determine at least one pending setpoint value based on the change, and the instructions that cause a processor to generate a pending rate response curve comprise instructions that cause a processor to generate a pending rate response curve based on the at least one pending setpoint value.

25. The computer-readable medium of claim 24, further comprising instructions that cause a processor to determine at least one pending optimization target value based on the change to at least one current curve value, wherein the instructions that cause a processor to generate a pending target rate histogram comprise instructions that cause a processor to generate a pending target rate histogram based on the at least one pending optimization target value.

26. The computer-readable medium of claim 25, wherein the instructions that cause a processor to determine a pending optimization target value based on a change to a current curve value comprise instructions that cause a processor to identify a pending optimization target value within a lookup table based on the magnitude of the change of the curve value.

27. The computer-readable medium of claim 15, further comprising instructions that cause a processor to:
receive data from the implantable medical device; and
display at least one of an atrial rate histogram, ventricular rate histogram, and actual sensor indicated rate histogram via the user interface based on the data.

28. The computer-readable medium of claim 27, wherein the instructions that cause a processor to display at least one of an atrial rate histogram, ventricular rate histogram, and actual sensor indicated rate histogram comprise instructions that cause a processor to display at least one of an atrial rate histogram, ventricular rate histogram, and actual sensor indicated rate histogram within the same window and at the same time as at least one of the current target rate histogram and a pending target rate histogram.

29. A device comprising:
a transceiver to communicate with an implantable medical device; and
a processor adapted to:
receive currently programmed rate response parameters and at least one currently programmed optimization target value from the implantable medical device via the transceiver,
display the currently programmed parameters and at least one target value via a user interface,
generate a current rate response curve which represents sensor indicated rate as a function of activity level based on the parameters, and a current target rate histogram which represent an estimate of percentage of time as a function of sensor indicated rate based solely upon the currently programmed parameters and at least one target value and not based upon a rate response signal generated in response to a patient undergoing a prescribed exercise test or predetermined regimen of physical exertion and without first reprogramming the implantable medical device, and
display the curve and the histogram via the user interface.

30. The device of claim 29, wherein the currently programmed rate response parameters include currently programmed rate limits and setpoint values, and the processor displays the currently programmed rate limits, determines current curve values based on the currently programmed setpoint values, and displays the current curve values.

31. The device of claim 30, wherein the processor generates the current rate response curve based on the currently programmed rate limits and setpoint values.

32. The device of claim 30, wherein the processor identifies the current curve values in a look-up table based on the currently programmed setpoint values.

33. The device of claim 29, wherein a currently programmed optimization target value comprises a target percentage of time for a sensor indicated rate to be within a range of rates.

34. The device of claim 33, wherein the processor generates a current target rate histogram by estimating the percentage of time that the implantable medical device causes the sensor indicated rate to be within a number of rate range bins based on the at least one currently programmed optimization target value.

35. The device of claim 29, wherein the processor receives a change made by a user to at least one of the currently programmed parameters via a user interface, generates a pending rate response curve and a pending target rate histogram based on the change, and displays the pending rate response curve and the pending target rate histogram via the user interface.

36. The device of claim 35, wherein the processor displays the current rate response curve and the pending rate response curve at the same time within a first window of the user interface, and displays the current target rate histogram and the pending target rate histogram at the same time within a second window of the user interface.

37. The device of claim 35, wherein the processor reprograms the implantable medical device based on the at least one changed parameter.

38. The device of claim 35, wherein the currently programmed rate response parameters include currently programmed setpoint values, and the processor determines current curve values based on the currently programmed setpoint values, displays the current curve values via the user interface, receives a change made by a user to at least one current curve value via the user interface, determines at least one pending setpoint value based on the change, and generates the pending rate response curve based on the at least one pending setpoint value.

39. The device of claim 38, wherein the processor determines at least one pending optimization target value based on the change to at least one current curve value, and generates the pending target rate histogram based on the at least one pending optimization target value.

40. The device of claim 39, wherein the processor identifies the pending optimization target value within a lookup table based on the magnitude of the change of the curve value.

41. The device of claim 29, wherein the processor receives data from the implantable medical device via the transceiver, and displays at least one of an atrial rate histogram, ventricular rate histogram, and actual sensor indicated rate histogram via the user interface based on the data.

42. The device of claim 41, wherein the processor displays at least one of an atrial rate histogram, ventricular rate histogram, and actual sensor indicated rate histogram within the same window and at the same time as at least one of the current target rate histogram and a pending target rate histogram.

* * * * *